United States Patent [19]

Regnery et al.

[11] Patent Number: 5,399,485
[45] Date of Patent: Mar. 21, 1995

[54] **METHODS AND COMPOSITIONS FOR DIAGNOSING CAT SCRATCH DISEASE AND BACILLARY ANGIOMATOSIS CAUSED BY *ROCHALIMAEA HENSELAE***

[75] Inventors: Russell L. Regnery; Burt E. Anderson, both of Tucker, Ga.

[73] Assignee: United States of America, Washington, D.C.

[21] Appl. No.: 822,539

[22] Filed: Jan. 17, 1992

[51] Int. Cl.$^6$ .................. G01N 33/569; C12Q 1/68; C07K 15/28
[52] U.S. Cl. .................. 435/7.32; 435/6; 436/811; 530/388.4; 530/387.1; 530/389.5; 530/391.1; 530/391.3
[58] Field of Search ............ 435/7.32, 6, 240.27, 435/252.1, 960; 530/388.4, 389.5, 391.1, 391.3, 387.1; 436/811

[56] References Cited

PUBLICATIONS

Regnery et al, "Serological response to *Rochalimaea henselae* antigen in suspected cat-scratch disease", The Lancet, 339:1443–1445 (Jun. 13, 1992).
Matthews et al, "Analytical strategies for the use of DNA probes", Anal. Biochem., 169:1–25 (1988).
LeBoit et al, Abstract #314, Laboratory Investigation, 58(1): p. 53A, (Jan. 1988).
Sevier et al, Clin. Chem., 27(11):1797–1806 (1981).
Anderson et al., *Amer. Soc. for Rickettsiology and Rickettsial Diseases*, p. 16, Apr. 13, 1991.
Regnery et al., *Amer. Soc. for Rickettsiology and Rickettsial Diseases*, p. 37, Apr. 13, 1991.
Brenner et al., *J. Clin. Micro.* 29:1299–1302, 1991.
O'Connor et al., *J. Clin. Micro.* 29:2144–2150, 1991.
Brenner et al., *J. Clin. Micro.* 29:2450–2460, 1991.
Cockerelle et al., *N. Eng. J. Med.* 324:1511–1512, 1991.
Birtles et al., *N. Eng. J. Med.* 325:1447–1448, 1991.
Relman et al., *N. Eng. J. Med.* 323:1573–1580, 1990.
Slater et al., *N. Eng. J. Med.* 323:1587–1593, 1990.
Schlossberg et al., *Arch. Intern. Med.* 149:1437–1439, 1989.
English et al., i JAMA. 259:1347–1352, 1988.
Angritt et al., *Lancet.* 1:996, 1988.

*Primary Examiner*—Carol E. Bidwell
*Attorney, Agent, or Firm*—Needle & Rosenberg

[57] ABSTRACT

The present invention relates to a method of diagnosing cat scratch disease and a method of diagnosing bacillary angiomatosis in a subject by detecting the presence of *Rochalimaea henselae* or an immunogenically specific determinant thereof in the subject. Also provided by the present invention is a vaccine comprising an immunogenic amount of a nonpathogenic *Rochalimaea henselae* or an immunogenically specific determinant thereof and a pharmaceutically acceptable carrier.

17 Claims, 3 Drawing Sheets

|  | | | |
|---|---|---|---|
| ROCHALI-MAEA HENSELAE | (19) | 10/34 | 16/32 | 8/32 |
| ROCHALI-MAEA VINSONII | 10.8 | (15) | 8/28 | 6/28 |
| ROCHALI-MAEA QUINTANA | 6.0 | 11.0 | (13) | 8/26 |
| RICKETT-SIA PROWAZEKII | 12.2 | 13.6 | 10.3 | (13) |

FIG.1

METHODS AND COMPOSITIONS FOR DIAGNOSING CAT SCRATCH DISEASE AND BACILLARY ANGIOMATOSIS CAUSED BY *ROCHALIMAEA HENSELAE*

BACKGROUND OF THE INVENTION

Cat scratch disease (CSD) has been the subject of considerable clinical and microbiologic interest for many years. An estimated 7,000 cases of cat scratch disease occur each year in the United States. Due to difficulty in diagnosing CSD and its potentially confusing clinical similarity with other disease syndromes, the number of actual cases of CSD in the United States may be closer to 70,000 per year. CSD is described as a subacute regional lymphadenitis temporally associated with the scratch or bite of a cat, and it occasionally results in meningoencephalitis.

Diagnosis of CSD has been a problem because the etiologic agent of the disease has not been previously identified. An unidentified bacillus has been visualized in biopsies from patients with CSD using Warthin-Starry stain but has resisted identification because of difficulties in obtaining an isolated culture. The etiologic agent of CSD has recently been proposed to be "*Afipia felis*" (Brenner et al., *J. Clin. Microbiol.* 29:2450-60, 1991). Despite these efforts, it has not been possible thus far to isolate or otherwise associate this agent with most persons suffering from cat scratch disease.

A clinically related disease, bacillary angiomatosis (BA), is a condition characterized by multiple tumors or swelling due to proliferation of the blood vessels. BA is often found in association with an immunocompromised condition, particularly HIV infection. An unidentified bacillus has been visualized in the angiomatous tissues using Warthin-Starry stain (Relman et al., *N. Eng. J. Med.* 323:1573-80, 1990). DNA extracted from the angiomatous tissues was shown to contain a fragment of 16S rRNA gene related to, but not identical to, the 16S rRNA gene of *Rochalimaea quintana*. This DNA was not obtained from a pure culture of the organism (Relman et al. 1990). These investigators were unable to isolate an infectious organism from patient tissues and, therefore, were unable to clearly associate the DNA sequences observed in tissues with an identifiable disease-causing organism. Neither the organism seen in these tissues nor the actual causative agent of the disease was identifiable.

Thus, despite intensive research and widespread effects of the diseases, the etiologic agent(s) of both CSD and BA have evaded identification. This invention describes the identification of an organism, named *R. henselae* herein, which is causative of both diseases.

SUMMARY OF THE INVENTION

The present invention relates to a method of diagnosing cat scratch disease and a method of diagnosing bacillary angiomatosis in a subject by detecting the presence of Rochalimaea henselae or an immunogenically specific determinant thereof in the subject. Also provided by the present invention is a vaccine comprising an immunogenic amount of a nonpathogenic *Rochalimaea henselae* or an immunogenically specific determinant thereof and a pharmaceutically acceptable carrier.

*Rochalimaea henselae, sp. nov.* is found to be a rickettsial-like organism associated with a variety of disease syndromes. A serologic test is presented for detection of humoral antibodies and human sera is evaluated for sero-positivity to Rochalimaea antigens. Data show that 1) humoral immune responses to *Rochalimaea* antigens are relatively specific, 2) healthy persons have a low but significant antibody prevalence to *R. henselae* antigen, and 3) 87.5% of persons diagnosed as having cat scratch disease by their physicians were identified as *R. henselae* seropositive. These data demonstrate that there is an excellent association between persons diagnosed as having cat scratch disease and infection with *R. henselae*.

BRIEF DESCRIPTION OF THE FIGURES

FIG. 1 shows the number of comigrating DNA fragments and the estimated percentage of sequence divergence among organisms related to *R. henselae*. Numbers in parentheses (along the diagonal) indicate the total number of fragments used in analysis of each species. Fractions in the upper right sector indicate the number of comigrating DNA fragments for each pair of species divided by the number of fragments present for both species. Numbers in the lower left sector correspond to the estimated percentage of sequence divergences.

DETAILED DESCRIPTION OF THE INVENTION

Figure 2:
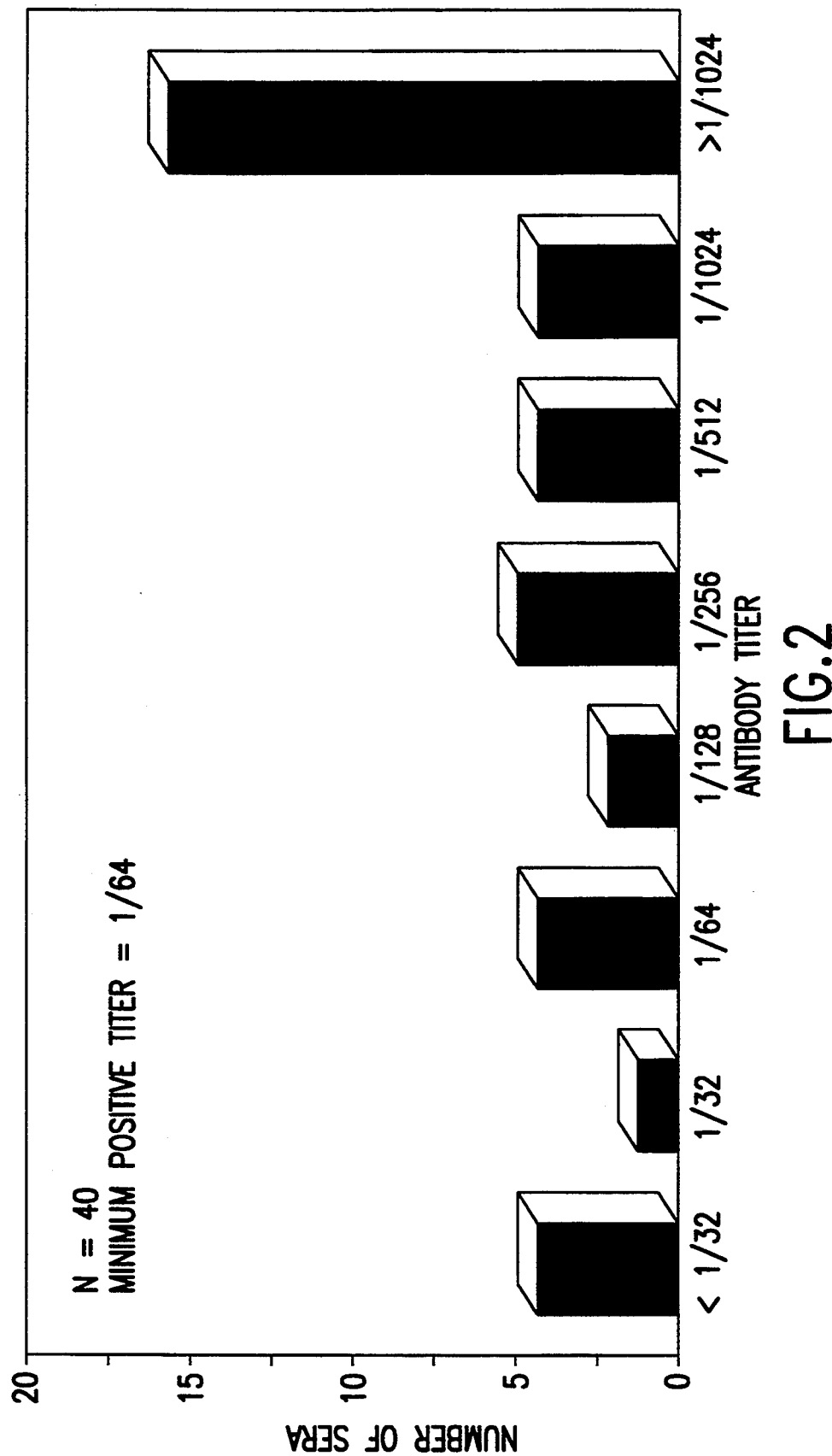
FIG. 2 shows the distribution of *R. henselae* specific antibody titers among persons diagnosed with cat scratch disease syndrome.

The present invention provides a method of diagnosing cat scratch disease in a subject comprising detecting the presence of *Rochalimaea henselae* or an immunogenically specific determinant thereof (hereinafter collectively referred to as "*R. henselae* antigen") in the subject. The subject can be a human or other animal. As used herein, an "immunogenically specific determinant" can be on an intact *R. henselae* or a fragment of *R. henselae*.

Given the subject discovery that the presence of *R. henselae* is associated with cat scratch disease, bacillary angiomatosis and splenic hepatic peliosis, many well-known methods of detecting a bacteria can be applied to detect *R. henselae* and diagnose a disease. In one example of the method of diagnosing cat scratch disease, the step of detecting *R. henselae* antigen is performed by contacting a fluid or tissue sample from the subject with an amount of a purified ligand, e.g. antibodies, specifically reactive with *R. henselae* antigen and detecting the reaction of the ligand with *R. henselae* antigen. As contemplated herein, the ligand can be an antibody, a fragment of an antibody or another reagent that has reactivity with the antigen. The fluid sample of this method can comprise any body fluid which would contain *R. henselae*, blood, plasma and serum. Other possible examples of body fluids include urine, sputum, mucus and the like.

In an alternative embodiment, the method of diagnosing cat scratch disease of the present invention can be such that the presence of *R. henselae* is determined by detecting the presence of an antibody from the subject which is specifically reactive with *R. henselae* antigen. The presence of antibody specifically reactive with *R. henselae* indicates the presence of infection by *R. henselae*. As used herein, the term "specifically reactive" denotes an antibody or other ligand that does not cross react substantially with any antigen other than the one specified, in this case, *R. henselae* antigen.

When the method of diagnosing cat scratch disease is by detecting the presence of an antibody specifically reactive with *R. henselae* antigen, the step of detecting the presence of an antibody specifically reactive to *R. henselae* antigen can, for example, include the steps of contacting a fluid or tissue sample from the subject with an amount of *R. henselae* antigen to react with an antibody specifically reactive with *R. henselae* antigen and detecting the reaction of the *R. henselae* antigen with the antibody. One method of conducting such a diagnosis is illustrated in Example 2.

In the diagnostic methods of the instant invention, the presence of *R. henselae* can also be determined by detecting the presence of a nucleic acid sequence specific for *R. henselae*. As more specifically exemplified below, a nucleic acid sequence specific for *R. henselae* can comprise nucleic acids coding for 16S ribosomal RNA subunit. Alternatively, a nucleic acid sequence specific for *R. henselae* can comprise nucleic acids coding for citrate synthase. It is apparent that a skilled artisan can apply the methods described herein for detecting the citrate synthase gene and the 16S ribosomal RNA gene to detect other nucleic acid sequences specific for *R. henselae*. Examples of other sequences specific for *R. henselae* can include the genes for heat shock protein, antigenic proteins and certain metabolic and synthetic enzymes. The specificity of these sequences for *R. henselae* can be determined by conducting a computerized comparison with known sequences, catalogued in GenBank, a computerized database, using the computer program Gap of the Genetics Computer Group, which searches the catalogued sequences for similarities to the gene in question.

Detecting the reaction of the ligand with *R. henselae* antigen can be facilitated by the use of a ligand that is bound to a detectable moiety. Such a detectable moiety will allow visual detection of a precipitate or a color change, visual deletion by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-strepavidin (for light or electron microscopy) and alkaline phosphatase (for biochemical detection by color change). The detection method and detectable moiety used can be selected from the list above or other suitable examples by the standard criteria applied to such selections (Harlow and Lane, *Antibodies: A Laboratory Manual*, Cold Spring Harbor Laboratory, Cold Spring Harbor, New York, 1988).

In the diagnostic methods of the present invention, the step of detecting the reaction of the ligand with *R. henselae* antigen can be further aided, in appropriate instances, by the use of a secondary antibody or other ligand which is reactive, either specifically with a different epitope or nonspecifically with the ligand or reacted antibody.

In the diagnostic method which detects the presence of an antibody specifically reactive with *R. henselae* antigen, the *R. henselae* antigen can be bound to a substrate and contacted by a fluid sample such as blood, plasma or serum. This sample can be taken directly from the patient or in a partially purified form. In this manner, antibodies specific for *R. henselae* antigen (the primary antibody) will specifically react with the bound *R. henselae* antigen. Thereafter, a secondary antibody bound to, or labeled with, a detectable moiety can be added to enhance the detection of the primary antibody. Generally, the secondary antibody will be selected for its ability to react with multiple sites on the primary antibody. Thus, for example, several molecules of the secondary antibody can react with each primary antibody, making the primary antibody more detectable.

Detecting methods such as immunofluorescence assays (IFA) and enzyme linked immunosorbent assays (ELISA) can be readily adapted to accomplish the detection of both *R. henselae* antigen and antibodies specifically reactive therewith. An example of an IFA protocol is provided in Example 2. The indirect immunocytochemical methods taught in Example 2 will be generally applicable for the detection of antigens or antibodies. An ELISA method effective for the diagnosis of cat scratch disease based on the detection of human IgG antibodies can, for example, be as follows: (1) bind the antigen (*R. henselae* antigen) to a substrate; (2) contact the bound antigen with a serum sample, containing antibodies reactive with *R. henselae* antigen, from a subject; (3) contact the above with an anti-human IgG antibody (secondary antibody) bound to a detectable moiety (e.g., horseradish peroxidase enzyme or alkaline phosphatase enzyme); (4) contact the above with the substrate for the enzyme; (5) contact the above with a color reagent; (6) observe color change in the presence of IgG antibody specifically reactive with *R. henselae* antigen. An indirect enzyme-linked immunosorbent assay (ELISA) for IgG antibodies against *R. henselae* is briefly as follows: Flat-bottomed 96-well polystyrene plates are coated with *R. henselae* or negative control antigen and allowed to incubate overnight. The next day, two-fold serial dilutions of test sera and 5 negative control sera, mouse anti-human IgG conjugated to horseradish peroxidase, and finally the substrate ABTS (2,2'-azino-di-[3-ethyl-benzthiazoline sulfonate]) are added to each well sequentially. Between each step, plates are incubated for 1 hour at 37° C. and then washed 3 times with 0.1% Tween 20 in phosphate-buffered saline (pH 7.4). Dilutions of sera are considered positive when the difference in absorbance between that serum specimen when tested with *R. henselae* antigen and the negative control antigen exceeds the mean plus 3 standard deviations of the 5 negative control sera tested with both *R. henselae* and negative control antigens.

A modification of the above ELISA effective for diagnosis of cat scratch disease and bacillary angiomatosis based on the detection of human IgM antibodies can be as follows: (1) bind an anti-human IgM antibody capable of reacting with a human IgM antibody to a substrate (antibody capture); (2) contact the bound antibody with a serum sample from a subject; (3) contact the above with *R. henselae* antigen; (4) contact the above with a rabbit anti-*R. henselae* antibody; (5) contact the above with an anti-rabbit antibody bound to a detectable moiety (e.g., horseradish peroxidase enzyme); (6) contact the above with substrate for the enzyme; (7) contact the above with a color reagent; (8) observe a color change in the presence of an IgM antibody specifically reactive with *R. henselae* antigen. For the IgM capture ELISA, flat-bottomed 96-well polystyrene plates are coated with goat anti-human IgM antibody, followed by serial two-fold dilutions of sera including 5 negative controls, *R. henselae* or negative control antigens, *R. henselae* hyperimmune rabbit antisera, and goat anti-rabbit conjugated to horseradish peroxidase and the substrate (ABTS). Between each step, plates are incubated for 1 hour at 37° C., and then washed 3 times with 0.1% Tween 20 in phosphate-buffered saline (pH 7.4). Dilutions of sera are considered positive when the difference in absorbance between that serum specimen when tested with R. henselae antigen and the negative control antigen exceeds the mean plus 3 standard deviations of the 5 negative control sera tested with both R. henselae and negative control antigens.

Another immunologic technique that can be useful in the detection of R. henselae infection utilizes monoclonal antibodies for detection of antibodies specifically reactive with R. henselae antigen. Briefly, sera from the subject is reacted with R. henselae antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular species since it is based on monoclonal antibody binding specificity.

A micro-agglutination test can also be used to detect the presence of R. henselae in a subject. Briefly, latex beads (or red blood cells) are coated with R. henselae antigen and mixed with serum from the subject, such that antibodies in the tissue or body fluids that are specifically reactive with R. henselae antigen crosslink with the antigen, causing agglutination. The agglutinated antigen-antibody complexes form a precipitate, visible with the naked eye. In a modification of the above test, antibodies specifically reactive with R. henselae antigen can be bound to the beads and antigen in the serum thereby detected. Other fluids of a subject can be effectively used.

In addition, as in a typical sandwich assay, the antibody is bound to a substrate and reacted with an R. henselae antigen. Thereafter, a secondary labeled antibody is bound to epitopes not recognized by the first antibody and the secondary antibody is detected.

The specific reagents and protocols for use in the detection methods described above and similar indirect immunocytochemical methods can be selected from those available in the art based on standard criteria (Harlow and Lane, *Antibodies: A Laboratory Manual*, Cold Spring Harbor Laboratory, Cold Spring Harbor, N.Y., 1988).

The instant invention also provides a method of diagnosing clinical bacillary angiomatosis in a subject by detecting the presence of R. henselae antigen in the subject. The step of detecting the presence of R. henselae can be accomplished in the same manner as stated above for the diagnosis of cat scratch disease.

The present invention further provides a kit for the diagnosis of cat scratch disease. Such a kit can be an ELISA kit and can comprise the substrate, antigen, primary and secondary antibodies when appropriate, and any other necessary reagents such as detectable moieties, enzyme substrates and color reagents as described above. The diagnostic kit of the present invention can alternatively be constructed to detect nucleic acid sequences specific for R. henselae antigen comprising the standard kit components such as the substrate and reagents such as those set forth in Example 1 for the detection of nucleic acid sequences. The diagnostic kit can, alternatively, be an IFA kit generally comprising the components and reagents described in Example 2 below. Because R. henselae infection can be diagnosed by detecting nucleic acids specific for R. henselae in tissue and body fluids such as blood and serum, it will be apparent to an artisan that a kit can be constructed that utilizes the nucleic acid detection methods taught herein. It is contemplated that the diagnostic kits will further comprise a positive and negative control test.

The particular reagents and other components included in the diagnostic kits of the present invention can be selected from those available in the art in accord with the specific diagnostic method practiced in the kit. Such kits can be used to detect R. henselae antigen and antibodies specifically reactive therewith in tissue and fluid samples from a subject and in cultures of microorganisms obtained from the tissue or fluids of a subject.

The kits of the instant invention can also be used in a method of diagnosing bacillary angiomatosis.

A nonpathogenic R. henselae antigen can be derived by modifying the R. henselae organism using standard techniques. For example, the whole cell antigen can be subjected to gamma irradiation to render the R. henselae nonpathogenic. Other standard methods of inactivating whole cell antigen include treatment with $\beta$-propriolactone or formalin (Harlow and Lane, *Antibodies: A Laboratory Manual*, Cold Spring Harbor Laboratory, Cold Spring Harbor, N.Y., 1988).

Alternatively, an immunogenically specific determinant of R. henselae can be isolated from the whole organism by chemical or mechanical disruption of the organism. For example, a carbohydrate moiety of R. henselae can be obtained by standard methods such as digesting R. henselae with a protease to remove protein moieties. The carbohydrate moieties thus obtained can be tested to determine their immunogenicity and specificity by the usual methods. Briefly, various concentrations of a putative inactivated (nonpathogenic) immunogenically specific determinant are prepared and administered to an animal and the immunological response (i.e., the production of antibodies) of an animal to each concentration is determined. The amounts of antigen or inactivated or modified-live organism administered depend on the subject, e.g. a human or a cat, the condition of the subject, the size of the subject, etc. Thereafter an animal so inoculated to the nonpathogenic antigen can be exposed to the pathogenic organism to test the potential vaccine effect of the immunogenically specific determinant. The specificity of a putative immunogenically specific determinant can be ascertained by testing sera or other fluid from the inoculated animal for cross reactivity with *Rochalimaea quintana*, a closely related species (Harlow and Lane, *Antibodies: A Laboratory Manual*, Cold Spring Harbor Laboratory, Cold Spring Harbor, N.Y., 1988).

Alternatively, a protein moiety of R. henselae can be obtained by treating the whole organism with an ionic detergent such as sodium dodecyl sulfate or a nonionic detergent such as Triton X-100 ($C_{34}H_6O_{11}$ average) or ethylphenyl-polyethylene glycol (NP-40, Shell Oil Company). The protein fragments so obtained can be tested for immunogenicity and specificity as described above. Other immunogenically specific determinants of R. henselae can be obtained by the standard methods described above.

The immunogenically specific determinant of this invention can be obtained by synthesizing a vector comprising a nucleic acid sequence encoding an immunogenically specific determinant of *R. henselae*. The vector can then be placed in a host wherein the immunogenically specific determinant of *R. henselae* will be synthesized. The selection of a nucleic acid sequence that encodes an immunogenically specific determinant can be accomplished by screening clone libraries of *R. henselae* DNA. Briefly, the *Rochalimaea* is lysed and the DNA extracted via standard procedure using 1% sodium dodecyl sulfate and proteinase K. The resulting DNA is then partially digested with restriction endonuclease EcoRI, size fractionated and gel purified (agarose gel electrophoresis), and cloned into lambda phage vector lambda zapII following standard procedures such as described in Maniatis et al. (*Molecular Cloning: A Laboratory Manual*, Cold Spring Harbor, N.Y., 1982). The recombinant plaques are screened for antigen production via ELISA with primary antibody being human or other non-human (e.g., feline) convalescent sera absorbed with an *E. coli* lysate. Antigen expressing clones are subcloned.

The subclones expressing *R. henselae* specific antigens are sequenced and corresponding synthetic peptides are constructed from the deduced amino acid sequence for use as diagnostic antigens or immunogens. Alternatively, recombinant antigens could be purified by affinity chromatography or high pressure liquid chromatography and the like.

The nonpathogenic *R. henselae* antigen of this invention can be used in the construction of a vaccine comprising an immunogenic amount of *R. henselae* antigen and a pharmaceutically acceptable carrier. This *R. henselae* antigen can be killed, modified live or immunogenic fragments of *R. henselae*. Alternatively, mixtures of intact *R. henselae* and immunogenic fragments can be used. The vaccine can then be used in a method of preventing cat scratch disease in a subject by administering the vaccine to the subject. The vaccine can also be used in a method of preventing bacillary angiomatosis in a subject by administering the vaccine to the subject. Furthermore, the fact that other disease syndromes are associated with *R. henselae* infection, means that such diseases can also be prevented by use of the vaccines of this invention. The prevention methods will work when the subject is a human, or likewise when the subject is a nonhuman animal, such as a cat.

The pharmaceutically acceptable carrier in the vaccine of the instant invention can comprise saline or other suitable carriers (Arnon, R. (Ed.) *Synthetic Vaccines* I:83-92, CRC Press, Inc., Boca Raton, Fla., 1987). An adjuvant can also be a part of the carrier of the vaccine, in which case it can be selected by standard criteria based on the particular *R. henselae* antigen used, the mode of administration and the subject (Arnon, R. (Ed.) *Synthetic Vaccines* I:93-103, CRC Press, Inc., Boca Raton, Fla., 1987). Methods of administration can be by oral or sublingual means, or by injection, depending on the particular vaccine used and the subject to whom it is administered.

It can be appreciated from the above that the vaccine can be used as a prophylactic or a therapeutic. Thus, subjects with the disease can be treated utilizing the vaccine. Further, through such vaccination the spread of disease between animals and humans can be prevented. For example, a cat or dog can be immunized, thereby preventing much of the exposure risk to humans.

Immunogenic amounts of *R. henselae* antigen can be determined using standard procedures. Briefly, various concentrations of a putative inactivated (nonpathogenic) immunogenically specific determinant are prepared, administered to an animal and the immunological response (i.e., the production of antibodies) of an animal to each concentration is determined.

Thus, the invention provides methods of preventing or treating an *R. henselae* infection and the associated disease by administering the vaccine to a subject.

Other compositions of this invention include a purified *R. henselae* bound to a ligand, e.g. an antibody. The term "purified" is used herein to describe antigens, antibodies and other ligands that are substantially free of other components of serum, blood or other body fluids, or other proteins associated with *R. henselae* in vivo.

A purified *R. henselae* antigen bound to a substrate and a ligand specifically reactive with *R. henselae* antigen are also contemplated. Such a purified ligand specifically reactive with *R. henselae* antigen can be an antibody. The antibody can be a monoclonal antibody obtained by standard methods. The monoclonal antibody can be secreted by a hybridoma cell line specifically produced for that purpose (Harlow and Lane, *Antibodies: A Laboratory Manual*, Cold Spring Harbor Laboratory, Cold Spring Harbor, N.Y., 1988). Likewise, polyclonal antibodies specifically reactive with *R. henselae* antigen are within the scope of the present invention. The polyclonal antibody can also be obtained by the standard immunization and purification protocols (Harlow and Lane, *Antibodies: A Laboratory Manual*, Cold Spring Harbor Laboratory, Cold Spring Harbor, N.Y., 1988).

The antibody can be bound to a substrate or labeled with a detectable moiety or both bound and labeled. The detectable moieties contemplated with the composition of the present invention are those listed above in the description of the diagnostic methods, including fluorescent, enzymatic and radioactive markers.

The compositions of the instant application further include an antibody reactive to a unique portion of an antibody specifically reactive with *R. henselae* antigen (primary antibody). The antibody reactive with the primary antibody is known as a secondary antibody, and can further comprise a detectable moiety. As described above, the reaction of the secondary antibody with the primary antibody specifically reactive with *R. henselae* antigen facilitates detection of the reaction of primary antibody with *R. henselae* antigen.

An isolated immunogenically specific determinant or fragment of *R. henselae* is also provided. The manner of obtaining such determinants is as described above for the construction of vaccines.

The following examples are intended to illustrate but not limit the invention. While they are typical of those that might be used, other procedures known to those skilled in the art may be alternatively employed.

EXAMPLE 1

Identification of *R. henselae*

A previously asymptomatic HIV-antibody positive, 40-year old man was admitted with a two month history of daily fever, extreme fatigue, anorexia, and loss of 10 Kg of weight. Five weeks after admission, blood cultures taken on the first and eighth day of hospitalization were reported positive for a *Rochalimaea*-like organism.

With the presumptive diagnosis of trench fever, the patient was started on a 21-day course of doxycycline (100 mg, twice a day); after 48 hours he defervesced. Blood, urine, bone marrow, and bronchoalveolar lavage fluid cultures remained negative for mycobacteria and fungi. Six weeks after discontinuation of therapy, fever, anorexia, and malaise recurred. Blood cultures drawn at this time were again positive for a *Rochalimaea*-like organism, and treatment with doxycycline for one month (same dose as above) was reinstituted with immediate and positive response. After a second relapse of fever, the patient completed two months of doxycycline (same dose as above). Repeated blood cultures taken in the subsequent 6 months have been negative and symptoms associated with his initial infection have not recurred. The organism isolated is hereinafter designated "Houston-1 isolate", which is considered the prototype isolate of *R. henselae*. This isolate is deposited with the American Type Culture Collection (12301 Parklawn Drive, Rockville, Md. 20852) under Accession No. ATCC 49882 (deposited Mar. 19, 1992).

A. Type Cultures

Two *Rochalimaea* isolates, representing two different recognized species, were obtained from the American Type Culture Collection (ATCC, Beltsville, Md.). *Rochalimaea quintana* (ATCC VR-358) and *R. vinsonii* (ATCC VR-152) were routinely cultivated at 35° C., 5% carbon dioxide atmosphere on tryptic soy agar, supplemented with 5% defibrinated sheep blood. *Rickettsia prowazekii*, isolate Breinl (ATCC VR-142), was cultivated in Vero cell cultures and cytoplasmic extracts containing rickettsiae were made by Regnery et al. (1990).

B. Growth Characteristics

1. Isolation and cultivation of the organism from patient's blood (Houston-1 isolate).

Blood from the patient was drawn either directly into a Wampole Isostat tube (Wampole Laboratories, Cranberry, N.J.) or simply into a Vacutainer tube containing EDTA (Becton Dickinson, Rutherford, N.J.); isolates were made using both starting preparations. The organism was reisolated from frozen (−85° C.) EDTA treated blood without significant loss of titer. Primary isolations were made on commercial brain heart infusion agar (BHIA) containing 5% sheep blood (BBL, Becton Dickinson, Cockeysville, Md.), tryptic soy agar (TSA) supplemented with 5% sheep blood (BBL), and heart infusion agar (HIA) containing 5% rabbit blood (BBL). Cultures were maintained at 35° C. in a humidified incubator containing 5% carbon dioxide. Bacteriological plates were routinely examined. As noted elsewhere, the Houston-1 isolate was cultivated from blood at various times during the course of the patients disease episode including after relapse of fever following cessation of antibiotic therapy. The key to obtaining isolated cultures of *R. henselae* is to allow the culture to grow long enough for this slow-growing organism to form detectable colonies.

Blood from the febrile patient, when cultured on either commercial BHIA-sheep blood, TSA-sheep blood, or HIA-rabbit blood, yielded characteristic colonies which were visible after 9–10 days incubation. The approximate titer of colony forming organisms in the patient's blood was 30 per milliliter after recrudescence of fever following the second course of antibiotic therapy. Primary colonies were deeply invaginated (cauliflower-like), firm, adherent, and tenaciously imbedded in the surface of the agar. All original individual colonies isolated from the patient's blood had similar morphologic and growth characteristics. Close inspection of subcultured plates revealed minute colony formation by 6 days after inoculation, although clear colony morphology was not evident at this time. After multiple passages of fresh colonies, incubation time to colony visualization decreased substantially and discrete colonies could be discerned after 3 to 4 days. The invaginated colony morphology became less pronounced after multiple, relatively rapid passages. Colony growth was not limited by incubation time, and colonies continued to grow progressively larger over a period of several weeks.

Several of these latter initial growth characteristics of the Houston-1 isolate were in contrast with those noted for the ATCC *Rochalimaea* type strains, which typically grew relatively rapidly without any delay in passaging, had shiny, smooth colonies, and were not similarly imbedded in the agar. Likewise, although *Rochalimaea* species isolates obtained from the ATCC proliferated rapidly on the surface of cultured cells, initial Houston-1 isolate material did not produce a similar generalized infection when inoculated on Vero cell monolayers, thus suggesting that co-cultivation with eucaryotic cells is not the method of choice for primary isolation. The Houston-1 isolate, after additional laboratory passages on solid medium (and perhaps more analogous to the ATCC type strains in terms of more extensive passage history), was not retested for the ability to grow rapidly on eucaryotic monolayers.

After reinoculation of the organism onto either chocolate agar or TSA-sheep blood, there was no growth in air at 22° C. or 42° C. but good growth at 30° and 35°. Colonies grew to slightly larger size when incubated in $CO_2$ (8%) at 35° C. than when cultured without added $CO_2$ at 35° C. Growth on subculture was also achieved on HIA-rabbit blood or TSA-sheep blood when plates were incubated in candle jars as previously described for other Rochalimaea isolates by Slater et al. (*N. Eng. J. Med.* 323:1587–1593, 1990). There was no growth observed on Sabouraud-dextrose medium. The growth characteristics of the freshly isolated Houston-1 agent contrasted with those of well-established type species of *Rochalimaea*. With passaging, colony morphology and speed of growth of the novel agent began to more closely resemble those of other *Rochalimaea*-type species. Although *R. henselae* appears to be a fastidious and slow growing organism, it can be cultivated by standard laboratory procedures. Relatively rapid growth (4 days between subculture) of the Houston-1 isolate was achieved by multiple passaging of fresh colonies shortly after they initially became visible. Semi-automated, clinical bacterial isolation procedures, which often rely on liquid media-based assays, in the absence of exogenous gaseous carbon dioxide, may not be suitable for cultivation/detection of primary *Rochalimaea* isolates. Moreover, such cultures are generally not maintained for an incubation period sufficient to detect growth of a primary isolate.

Preliminary attempts to cultivate the Houston-1 isolate in stationary, liquid media did not produce turbid suspensions of individual organisms; however, the blood agar plate-derived inoculum material appeared to act as foci for growth of limited numbers of large cohesive aggregates. Reinoculation of agar-grown organisms into Bactek 660 6A or 7A bottles (Becton Dickinson, Cockeysville, Md.) did not result in sufficient growth to change the growth index as compared to uninfected controls.

2. Additional Rochalimaea isolates.

Four *Rochalimaea*-like isolates, previously submitted to the CDC for microbial identification were compared with the Houston-1 isolate and recognized *Rochalimaea* species. Two of these isolates were recovered from patients in Oklahoma, one isolate originated in a patient who apparently acquired his illness in Arkansas, and a fourth isolate which originated in San Diego County, California. This last isolate currently represents one of the first *Rochalimaea* isolates, that we are aware of, that has been made in recent years as well as one of the first isolates reported from an HIV-infected individual (November, 1986).

C. Clinical Biochemical Analysis

Biochemical tests were performed by standard methods (Lennette et al., *Manual of Clinical Microbiology*, 14th Ed., Amer. Soc. for Microbiology, Washington, D.C., 1985) and using the RapID ANA II System which tests for the presence of preformed enzymes (Innovative Diagnostic Systems, Inc., Atlanta, Ga.). Tests for motility included observation of growth characteristics in motility agar and direct observation of bacilli with dark field microscopy. Presence of catalase was tested for by emulsifying a colony in hydrogen peroxide and checking for the presence of microscopic bubbles formed under a cover slip. The presence of oxidase was tested for using tetramethyl-p-phenylenediamine.

Except for the production of peptidases, the Houston-1 isolate was biochemically inert when tested by typical clinical procedures. The RapID ANA II system, designed primarily for the clinical identification of anaerobic organisms by detection of specific preformed enzymes, is also useful for the identification of difficult to identify aerobic organisms. The RapID ANA II system, when used for analysis of the Houston-1 isolate, detected a limited number of enzyme-substrate cleavage reactions which included the cleavage of leucylglycine, glycine, proline, phenylalanine, arginine, and serine resulting in an identification number 000671. No known microbe is currently associated with this identification number, however, members of the genus *Rochalimaea* are not yet part of the commercial diagnostic database (*Rapid ID ANA II Code Compendium*, Innovative Diagnostic Systems, Atlanta, Ga., 1989). Negative clinical assays included those testing for catalase, urease, esculin hydrolysis, motility, nitrate reduction, and oxidase.

D. Staining and Morphologic Characteristics

Four day-old cultures of the Houston-1 isolate were prepared for microscopy by flooding a blood agar plate containing the colonies with phosphate-buffered saline (PBS) and then gently sweeping adherent colonies off the agar surface with a bacteriological loop. A small aliquot of this material was placed directly on a clean microscope slide, heat-fixed, and stained with Gimenez stain. Other material was fixed with glutaraldehyde and prepared for electron microscopy. Briefly, the glutaraldehyde fixed material was filtered onto a Nucleopore filter (0.2 um pore size, Nucleopore Corp., Pleasanton, Calif.) and washed three times with Sorenson's buffer (pH 5.0). The filtered material was treated in 1% osmium tetroxide for 2 hours and again washed three times with Sorenson's buffer. The specimens were dehydrated in a graded series of increasing concentrations of ethanol (30% to 100%). The dehydrated specimens were immersed in hexamethyldisilizane (Polysciences, Inc., Warrington, Pa.) for 2 hours and then dried in a desiccator overnight. Finally, the specimens were placed on a stub, sputter coated with gold, and observed with a Philips (model 515) scanning electron microscope.

Rapidly proliferating organisms from four day-old cultures, obtained after several subpassages, stained readily with Gimenez histological stain. Organisms so stained appeared as small red bacilli, often slightly curved. Organisms obtained from older, but still quite viable colonies, resisted uptake of Gimenez stain. The material which was successfully used for light microscopy was also prepared for and observed using a scanning electron microscope. As with the Gimenez-stained material, and the observations of growth habits noted during various culturing experiments, the organisms viewed with the scanning electron microscope appeared to form cohesive aggregates, with relatively few organisms existing freely. The average size of organisms visualized was approximately 2 $\mu$m in length by 0.5 to 0.6 $\mu$m in width. All organisms observed within individual microscopic preparations, which presumably include the products of multiple generations, appeared to be relatively uniform in size.

E. Fatty Acid Analysis

Whole cell fatty acid analysis was performed on *R. henselae, sp. nov.* (Houston-1) cultures incubated at 35° C. in air and harvested after four days growth on chocolate agar. Fatty acid methyl esters were chromatographed on a Hewlett Packard series II 5890 gas chromatograph (Miller, L., T. Berger, "Bacterial identification by gas chromatography of whole cell fatty acids," Hewlett-Packard application note 228-41, Hewlett-Packard, Avondale, Pa., 1985) and identified using a computer-assisted comparison of retention times of the sample with that of a standard mixture (Microbial-ID, Newark, Del.).

The major fatty acids observed after whole cell fatty acid analysis of the Houston-1 isolate were octadecenoic acid ($C_{18:1}$, 54–56%), octadecanoic acid ($C_{18:0}$, 18–20%), and hexadecanoic acid ($C_{16:0}$, 17%). The absence of other detectable fatty acids excluded identification of almost all other bacteria except members of the genus *Brucella*. This fatty acid pattern was similar to that observed with *R. quintana* and other recent *Rochalimaea*-like isolates (Slater et al., *N. Eng. J. Med.* 323:1587–1593, 1990).

F. 16S rRNA Gene Sequence Analysis

1. DNA extraction, amplification and cloning.

DNA for polymerase chain reaction (PCR) amplification was extracted from pure cultures of *R. quintana*, *R. vinsonii*, and *R. henselae* (Houston-1 isolate) using sodium dodecyl sulfate (SDS)/proteinase K lysis followed by phenol/chloroform extraction as previously described (Sambrook et al., *Molecular Cloning: A Laborabory Manual*, 2nd Ed., Cold Spring Harbor Laboratory, Cold Spring Harbor, N.Y., 1989). The resulting aqueous phase was concentrated using a Centricon 30 concentrator (Amicon Corp., Danvers, Mass.) and washed three times with ml of TES (10 mM Tris, pH 8.0; 1 mM EDTA; 10 mM NaCl).

PCR amplification was performed using a thermal cycler and GeneAmp reagents (Perkin Elmer-Cetus, Norwalk, Conn.). Two pairs of "universal," degenerate primers known to amplify approximately 92% of the 16S ribosomal RNA gene, as two separate PCR products, from all eubacteria previously studied were used to prime PCR synthesis of products that were subsequently used for cloning and sequence analysis. The 5' end of each primer was modified to contain unique restriction endonuclease sites to facilitate cloning. Each sample was amplified for three cycles at: 94° C. 1 min; 48° C., 2 min; 66° C., 1 min 30 s, followed by 27 cycles at: 88° C., 1 min; 52° C., 2 min; 68° C., 1 min 30 s The resulting PCR products were isolated from a 1.0% agarose gel and cloned into pUC 19 (Sambrook et al. 1989). Clones were sequenced using double-stranded sequencing with T7 DNA polymerase (SEQUENASE, U.S. Biochemicals, Cleveland, Ohio). Each isolate was amplified, cloned, and sequenced at least twice to prevent the reading of PCR incorporation errors; if discrepancies were detected, a third, independent sequence was produced. Great care was taken not to introduce contaminating bacterial DNA into the PCR reactions using the universal primers because of their broad range of amplification. GenBank accession numbers for the respective 16S rRNA gene sequences are as follows: R. quintana, M73228; R. vinsonii, M73230; R. henselae (submitted as R. americana), M73229.

Universal primers allowed amplification of approximately 1400 nucleotides of the rRNA gene sequence as two separate PCR products. 767-base pair (bp) products, corresponding to the 5' half of the 16S rRNA gene, produced using primers EC11 and EC12 (modified versions of POmod and PC3mod primers used by Wilson et al., J. Clin. Microbiol. 28:1942–1946, 1990) were observed when the Houston-1 isolate, R. quintana and R. vinsonii were amplified. No product was observed when these primers were used to amplify a negative control containing no DNA template. Similarly, a 737 bp product corresponding to the 3' half of the 16S rRNA gene, produced with primers EC9 and EC10 (modified versions primers P3mod and PC5 used by Wilson et al. 1990) was seen when using Houston-1 isolate, R. quintana, R. vinsonii. No PCR product was seen in the no DNA control. These PCR products were cloned and sequenced.

2. DNA sequencing

The 16S rRNA gene sequences used for comparison and alignment were obtained by taking a consensus of three independent sequences for each cloned PCR product. The first and second sequences obtained for the Houston-1 isolate had three nucleotides in disagreement, and the first and second sequences for R. vinsonii had two ambiguities. In both cases a third sequence agreed with one of the two previous sequences at these ambiguous positions and was taken as the consensus. The occasional disagreement among sequences was assumed to be the result of polymerase-nucleotide incorporation errors. The entire sequence was used for alignment using the Gap program of the Genetics Computer Group. The sequence of the Houston-1 isolate was compared with 16S rRNA gene sequences on file with GenBank and showed the greatest homology with R. quintana (98.7%) and lesser homologies with 16S rRNA gene sequences from organisms more distantly related (Table 1).

In our laboratory we sequenced the 16S rRNA gene from R. quintana (Fuller strain) and found it to differ slightly from the sequence previously reported by Weisberg et al. (Science 230:556–558, 1985) and obtained from GenBank. Using our data, we found the 16S rRNA gene sequence from the Houston-1 isolate to be 98.7% related to R. quintana and 99.3% related to the R. vinsonii. The R. quintana and R. vinsonii sequences were found to be 98.9% related. The 0.7% 16S rRNA gene sequence divergence seen between the Houston-1 isolate and R. vinsonii is greater than the 0.5% divergence reported for Rickettsia prowazekii and Rickettsia typhi. These two species of Rickettsia are clearly distinct species among the order Rickettsiales, to which Rochalimaea belong.

The partial 16S rRNA gene sequence determined by Relman et al. (1990) (GenBank Acc. #M59459) for the putative etiologic agent of BA was found to be identical to the corresponding portion of the 16S rRNA gene sequence obtained from the Houston-1 isolate of R. henselae, sp. nov. (Table 1). Partial 16S rRNA gene sequences obtained from one of the Oklahoma isolates are identical to 16S rRNA gene sequences obtained from the Houston-1 isolate. These completely homologous sequences indicate that the causative agents are one and the same species. The variation between 16S rRNA gene sequences noted between the Houston-1 isolate and other type species of Rochalimaea (Table 1) indicates that the Houston-1 isolate represents a new species within the genus Rochalimaea.

Thus, the nucleic acids encoding the 16S rRNA subunit are specific for R. henselae and can be used to detect the presence of R. henselae.

TABLE 1

Relatedness between the Houston-1 isolate 16S rRNA gene and various enbacteria

| Species[a] | % Homology with Houston-1 Isolate Rochalimaea henselae |
|---|---|
| BA-TF[b] | 100.0 |
| Rochalimaea vinsonii | 99.3 |
| Rochalimaea quintana | 98.7 |
| Bartonella bacilliformis | 95.6 |
| Brucella abortus | 94.0 |
| Cat scratch fever agent (AFIP) | 87.9 |
| Rickettsia rickettsii | 84.9 |
| Ehrlichia risticii | 84.9 |

[a]The entire 16S rRNA gene sequence (when available) was used for alignment. The R. henselae, Houston-1 isolate, R. vinsonii, and R. quintana sequences were determined in our laboratory, all other sequences were obtained from GenBank.
[b]Partial 16S rRNA gene sequence from Relman et al. (1990).

G. Citrate Synthase Gene PCR/RFLP Analysis

Restriction-endonuclease length polymorphism (RFLP) analysis was applied to PCR-amplified DNA, which was primed with nondegenerate oligonucleotides previously demonstrated to initiate synthesis of PCR products approximately 381 nucleotides long from a portion of the rickettsial citrate synthase gene (Regnery et al., J. Bacteriol. 173:1576–1589, 1991). Chromosomal DNA from Rickettsia prowazekii was used as a positive control for PCR synthesis and digestion; controls containing no DNA template were always included in PCR amplifications.

1. DNA digestion and electrophoresis.

RFLP analysis-of specific genes, amplified by the PCR technique, is useful for identifying rickettsial genotypes and species. Oligonucleotides, previously demonstrated to be suitable for priming PCR amplification of a portion of the citrate synthase genes from nearly all rickettsial species, as well as from R. quintana, were tested for their ability to prime DNA amplification from DNA purified from the Houston-1 isolate and R. vinsonii. PCR products were readily produced using conditions comparable to those previously reported. Briefly, PCR amplification was accomplished in 100-μl volumes, using the protocols supplied with the GeneAmp DNA amplification reagent kit (Perkin-Elmer Cetus, Norwalk, Conn.). Typically, 1 μl of undiluted cytoplasmic extract DNA was used as PCR template. DNA amplification was done in a Perkin-Elmer Cetus DNA Thermal Cycler, using 35 cycles of denaturation (20 s at 95° C.), annealing (30 s at 48° C.), and extension (2 min at 60° C.).

PCR amplification of DNA was verified by rapid agarose electrophoresis of a small amount of PCR product. Restriction and endonuclease digestion was done with 20 μl of PCR reaction mixture, following standard techniques (Sambrook et al. 1989) and incubations were at 37° C. All restriction endonucleases were obtained from New England BioLabs, Beverly, Mass. After addition of dye-Ficoll loading mixture (Sambrook et al., 1989), the digested reactions were loaded on 1.5 mm thick, 8% polyacrylamide vertical gels (Bio-Rad Laboratories, Richmond, Calif.) made by standard procedures (Sambrook et al., 1989). Gels were run at 80 V for 4 h in simple vertical electrophoresis chambers (Bethesda Research Laboratories, Life Technologies, Inc., Gaithersburg, Md.). The gels were then stained with ethidium bromide prior to illumination on a UV light source (365 nm; Spectronic Corp., Westbury, N.Y. and photographed with Polaroid type 655 P/N film (Polaroid Corp., Cambridge, Mass.).

Digested DNA fragments were separated and analyzed using standard electrophoretic protocols and methods previously described by Regnery et al. (1991). The number of comigrating DNA fragments, observed between homologous PCR/RFLP digests of two or more isolates, were counted. Data from the number of comigrating DNA fragments were used to derive estimates of sequence relatedness by methods described by Upholt (*Nucleic Acids Res.* 4:1257–1265, 1977) and subsequently used by others to estimate sequence divergence between related bacteria.

All three of the uncut Rochalimaea citrate synthase PCR products were slightly larger (approximately 400 bp) than those produced for members of the genus *Rickettsia* (approximately 381 bp). Variation was noted between the sizes of PCR-amplified citrate synthase products obtained from different *Rochalimaea* isolates. PCR-amplified products were digested with seven restriction endonucleases and subjected to polyacrylamide gel electrophoresis. Obvious differences were seen in many of the digest patterns of PCR-amplified citrate synthase sequences from the various isolates; PCR/RFLP analysis allowed for rapid differentiation of other isolate genotypes.

The numbers of DNA fragments produced by digestion of the PCR-amplified, citrate synthase-specific DNA with seven restriction endonucleases are tabulated in FIG. 1, together with the number of comigrating fragments. Estimates of sequence divergence derived by numerical analysis of the percentage of comigrating fragments illustrate that all of the isolates examined have substantial inferred citrate synthase sequence divergence (6 to 11%) equalling or exceeding similar estimates for citrate synthase sequence divergence among recognized rickettsial species (e.g., 2 to 6%).

PCR/RFLP analysis clearly differentiated *R. henselae, sp. nov.,* genotype from that of either *R. quintana* or *R. vinsonii.* Multiple restriction-endonuclease digests of the citrate synthase-specific PCR products from other *Rochalimaea*-like isolates from Oklahoma (two isolates), Arkansas (one isolate), and Southern California (one isolate) demonstrated that all of the isolates studied are identical to one another, and *R. henselae* (Houston-1 isolate), according to the PCR/RFLP methods applied herein.

It is clear that in addition to cat scratch disease and bacillary angiomatosis the disease spectrum of this organism may be variable and include a syndrome of fever and bacteremia and bacillary peliosis hepatis. Thus, the nucleic acid methods described herein can be used to detect the presence of *R. henselae* associated with these disease syndromes.

EXAMPLE 2

Serological Methods

An immunofluorescent assay (IFA) test was developed to detect antibodies specifically reactive with *R. henselae* antigen in order to begin to assess distribution and prevalence of infection, and also to help define the full spectrum of *R. henselae*-induced disease. Infectious organisms were rendered nonpathogenic by inactivation by gamma irradiation.

A. Preparation of *R. henselae* antigenic determinant

*R. henselae* bacilli cultivated on erythrocyte-enriched agar media, and then kept in solution, tend to auto-agglutinate as previously described; this clumping obstructs the production of a well dispersed IFA antigen. Inhibition of auto-agglutination was achieved by cocultivation of *R. henselae* with Vero cells to which individual *Rochalimaea* organisms avidly adhered. Briefly, *R. henselae* cells are cultured in liquid medium with Vero cells for 4 days. After decanting most of the liquid medium, glass beads are added to the culture flask and gently agitated in the remaining medium. This agitation with beads loosens the Vero cells and their adherent *R. henselae* cells from the flask walls. The R. henselae cells complexed with the Vero cells are then inactivated (rendered nonpathogenic) by gamma irradiation. Antigen and antisera were prepared for IFA testing by standard techniques.

B. Preparation of antisera (antibodies)

Briefly, the *R. henselae* antigen obtained from isolated *R. henselae* cultures and suspended in PBS is inoculated into a rabbit to cause the rabbit to produce antibodies specifically reactive with the antigen. A blood sample from the animal is taken and red blood cells are removed to obtain antisera. The serum containing *R. henselae* antibodies is then subjected to ammonium sulfate to precipitate gamma globulins (IgG) out of the antiserum.

C. IFA

The IFA of this example is conducted briefly as follows: The Vero cell-associated *R. henselae* antigenic determinant prepared above is spotted into a well of a 12-well microscope slide and a spot of *R. quintana* is placed in the paired well as a control. The spots are air dried and then acetone fixed for 10 minutes. Serial dilutions of the antisera being tested (e.g. 1/32, 1/64, etc., dilution endpoint) are placed in the paired wells with the antigen. The slides are then incubated in a moist chamber at 37° C. for 30 minutes and thereafter washed 3 times with PBS, rinsed with distilled water and air dried. Fluorescein labeled goat antihuman IgG is then spotted into each well, and the slides incubated, washed, rinsed and dried as above. Buffered glycerol is added to the wells for optical enhancement and the slides are then analyzed by fluorescence microscopy to detect the presence of antibody specifically reactive with R. henselae antigen.

In an alternative method, the *R. henselae* specific antibody purified above can be directly labeled with a detectable moiety such as fluorescein (Harlow and Lane, *Antibodies: A Laboratory Manual*, Cold Spring Harbor Laboratory, Cold Spring Harbor, N.Y., 1988).

In all IFA determinations, antisera from humans with culture-confirmed *R. henselae* or *R. quintana* infections were used as positive controls.

Sera from 40 patients with suspected cat scratch disease were evaluated by IFA for reactivity with *R. henselae* antigen. Thirty-five (87.5%) patients had antibody titers to *R. henselae* that were equal to, or exceeded, 1/64 serum end-point dilution (FIG. 2). Many patients had sera with titers exceeding 1/1024. Sera collected during acute and convalescent phases of illness were available from several patients. Of five sets of paired sera that had different titers and included at least one specimen with a titer equal to, or exceeding, 1/64, three demonstrated four-fold rises or falls in antibody titer. Three additional paired sets of sera could not be evaluated for change in titer because both sera had antibody specifically reactive with *R. henselae* antigen of, or exceeding, a titer of 1/1024 (the maximum titer assayed). Eight of the sera with a titer of, or exceeding, 1/64 also had low antibody titers to *R. quintana* which did not exceed 1/32. In each of these sera, the titer of antibody specifically reactive with *R. henselae* exceeded the titer to R. quintana by at least four-fold.

Figure 3:
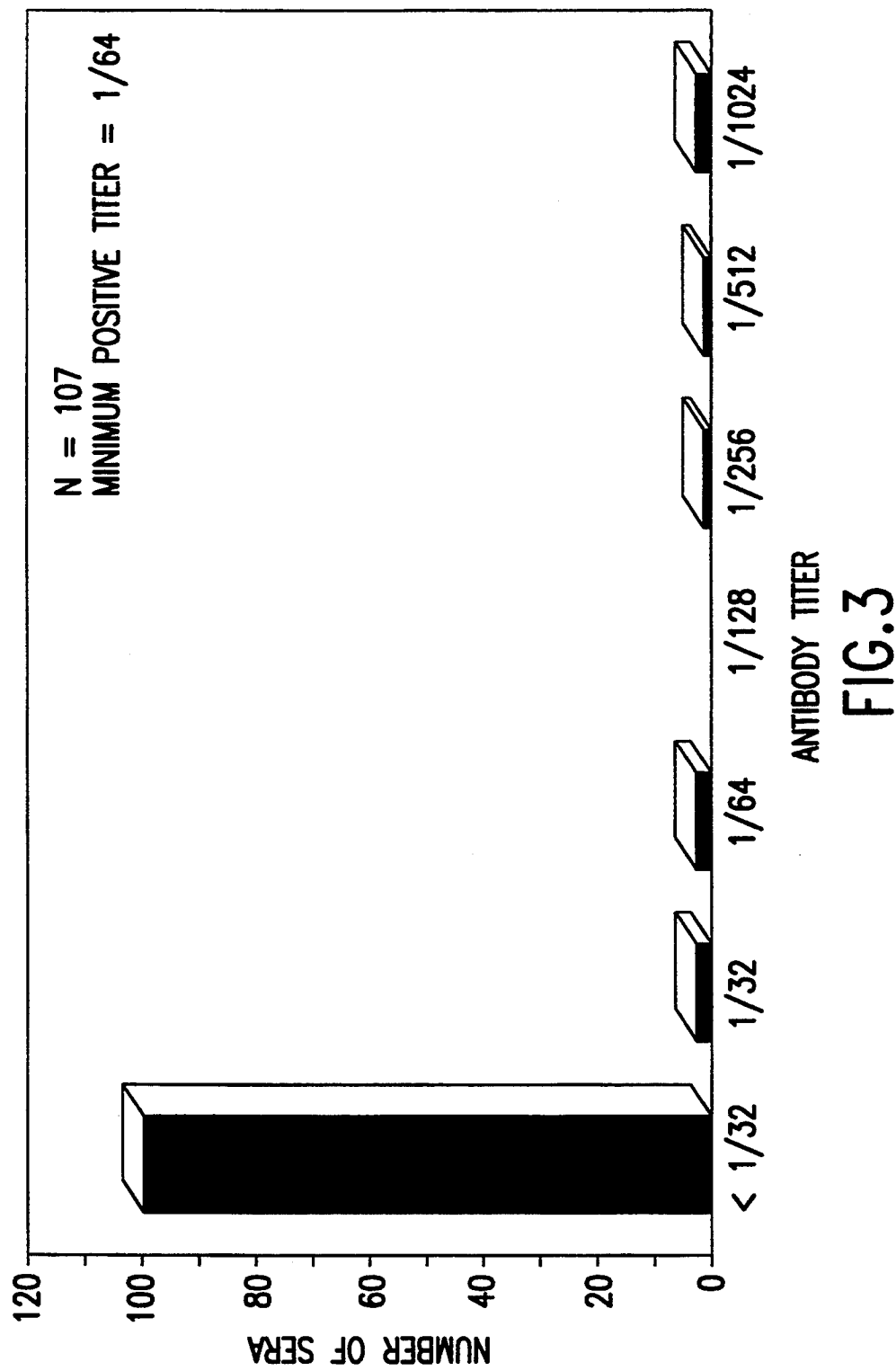
FIG. 3 shows the distribution of *R. henselae* specific antibody titers among healthy persons.

107 sera collected from persons who identified themselves as healthy individuals were obtained from a contract vendor (Worldwide Biologics, Cincinnati, Ohio). When these sera were tested by IFA for antibody reactive with *R. henselae* and *R. quintana*, 101 (94%) had titers less than 1/64 (FIG. 3). Of the six sera that had antibody titers to *R. henselae* antigen equal to or greater than 1/64, three had considerably elevated antibody titers (i.e., 1/512 and 1/1024). Antibody titers to *R. quintana* exceeding 1/16 were not detected among the serum donors.

Sera from persons with a variety of diseases were evaluated for the presence of possible antibodies specifically reactive with *R. henselae*. Titers less than or equal to 1/64 were detected in two of ten persons with brucellosis, however, the two low level positive serologic responses did not correlate with increasing titers of antibody to *Brucella abortus* as detected by microagglutination. One of three sera from patients with Lyme disease had a titer of 1/64 to *R. henselae*. Sera from patients with tularemia and sera from patients with *Yersinia entercolitica* infections did not show antibody titers to *R. henselae* that were in equal to or greater than 1/64. A number of other reference human antibodies used as reagents in diagnostic kits were evaluated with the *R. henselae* IFA test. None of these sera showed a titer of antibody for *R. henselae* at or above 1/64. The reference sera included human antisera to: *Mycoplasma pneumoniae, Treponema pallidum, Coxiella burnetii, Ehrlichia chaffeensis,* chlamydia group, spotted fever group rickettsiae, typhus group rickettsiae, varicella zoster, influenza type A, adenovirus, dengue virus type 2, herpes simplex, coxsackievirus group A, poliovirus type 2, cytomegalovirus, rubella, human immunodeficiency virus type I, as well as alpha-fetoprotein and rheumatoid factors.

Sera containing high-titered human antibody specifically reactive with *R. henselae* and antibodies for *R. quintana* did not react with "*A. felis*" antigen in the IFA test. Hyperimmune rabbit antisera and monoclonal antibodies directed against "*A. felis*" antigen were not reactive with *R. henselae* whole cell antigen.

High titered *R. quintana* antibody (1/1024 dilution endpoint) obtained from a human volunteer infected with *R. quintana* yielded no discernable reaction with *R. henselae* antigen (<1/16 dilution endpoint). Similarly, minimal (<1/32 dilution endpoint) *R. quintana* antibody titers were noted when high titered (e.g. >1/1024 dilution endpoint) serum was used from a culture positive *R. henselae* patient.

Thus, it is seen that the human serologic responses to *R. henselae* and *R. quintana* antigens, as assayed in the IFA test, are species-specific and it is unlikely that the antibody reactions observed with *R. henselae* antigen were due to antigenic stimulation by any species other than *R. henselae*.

There was a low prevalence of significantly elevated levels of antibody specifically reactive with *R. henselae* found among apparently healthy serum donors, indicating that *R. henselae* infection may be relatively common.

Out of 40 patients clinically diagnosed with cat scratch disease, 35 (87.5%) had sera antibody titers to *R. henselae* antigen that equaled or exceeded 1/64 and several paired sets of sera showed four-fold changes in titer. This method of detecting *R. henselae* antigen or antibodies specifically reactive therewith provides a useful diagnostic tool for identification of patients with cat scratch disease and thereby reduces reliance on clinical diagnosis alone, use of non-pharmaceutically approved CSD skin test antigen preparations, and need for surgical biopsy.

The method of diagnosing cat scratch disease exemplified herein can be applied equally effectively to the diagnosis of bacillary angiomatosis, because an etiologic agent of both diseases is *R. henselae*. Also, because *R. henselae* infection is associated with other disease syndromes, such as a syndrome of fever and bacteremia and bacillary peliosis hepatis, the serological, immunocytochemical, cytological and nucleic acid detection methods described above can be effectively used to diagnose these diseases.

It should be understood that the foregoing relates only to preferred embodiments of the present invention and that numerous changes and modifications may be made therein as described in the following claims.

What is claimed is:

1. A method of diagnosing cat scratch disease or the previous existence of cat scratch disease in a subject, comprising detecting the presence of *Rochalimaea henselae* in the subject, and correlating the presence of *Rochalimaea henselae* with the presence of cat scratch disease in the subject.

2. The method of claim 1, wherein the detecting step comprises the steps of:
   a. contacting a fluid or tissue sample from the subject with a detectable amount of an antibody or antigen-binding fragment thereof that specifically binds with *Rochalimaea henselae;* and
   b. detecting specific binding of the antibody with *Rochalimaea henselae.*

3. The method of claim 1, wherein the presence of *Rochalimaea henselae* is determined by detecting the presence of an antibody in the sample from the subject that specifically binds with *Rochalimaea henselae.*

4. The method of claim 3, wherein the step of detecting the presence of an antibody that specifically binds with *Rochalimaea henselae* comprises the steps of:

a. contacting an antibody-containing fluid or tissue sample from the subject with an amount of isolated *Rochalimaea henselae* or an immunogenic fragment thereof to specifically bind with the antibody; and b. detecting the specific binding of the *Rochalimaea henselae* with the antibody.

5. The method of claim 1, wherein the presence of *Rochalimaea henselae* is determined by detecting the presence of a nucleic acid specific for *Rochalimaea henselae*.

6. The method of claim 1, wherein the subject is a human.

7. A method of diagnosing bacillary angiomatosis or the previous existence of bacillary angiomatosis in a subject comprising detecting the presence of *Rochalimaea henselae*, and correlating the presence of *Rochalimaea henselae* with the presence of bacillary angiomatosis in the subject.

8. The method of claim 7, wherein the detecting step comprises the steps of:

a. contacting a fluid or tissue sample from the subject with a detectable amount of an antibody or antigen-binding fragment thereof that specifically binds with *Rochalimaea henselae;* and b. detecting the specific binding of the antibody with *Rochalimaea henselae.*

9. The method of claim 7, wherein the presence of *Rochalimaea henselae* is determined by detecting the presence of an antibody in the sample from the subject that specifically binds with *Rochalimaea henselae.*

10. The method of claim 9, wherein the step of detecting the presence of an antibody that specifically binds with *Rochalimaea henselae* comprises the steps of:

a. contacting an antibody-containing florid or tissue sample from the subject with an amount of isolated *Rochalimaea henselae* or an immunogenic fragment thereof to specifically bind with the antibody; and b. detecting the specific binding of the *Rochalimaea henselae* with the antibody.

11. The method of claim 7, wherein the presence of *Rochalimaea henselae* is determined by detecting the presence of a nucleic acid specific for *Rochalimaea henselae.*

12. The method of claim 7, wherein the subject is a human.

13. A purified antibody or antigen-binding fragment thereof that specifically binds with *Rochalimaea henselae.*

14. The antibody of claim 13, wherein the antibody is a monoclonal antibody.

15. The antibody of claim 13, bound to a substrate.

16. The antibody of claim 13, wherein the antibody is labeled with a detectable moiety.

17. The antibody of claim 16, wherein the detectable moiety is fluorescent.

* * * * *